US00PP25596P3

(12) United States Plant Patent
Klemm et al.

(10) Patent No.: US PP25,596 P3
(45) Date of Patent: May 26, 2015

(54) ***OSTEOSPERMUM* PLANT NAMED 'KLEOE12190'**

(50) Latin Name: ***Osteospermum ecklonis* Norl.**
Varietal Denomination: KLEOE12190

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmhH & Co. KG, Stuttgart (DE)

( * ) Notice: Subject to any disclaimer, the term of this patent is extended or adjusted under 35 U.S.C. 154(b) by 57 days.

(21) Appl. No.: 13/986,435

(22) Filed: May 2, 2013

(65) Prior Publication Data

US 2014/0331373 P1 Nov. 6, 2014

(51) Int. Cl.
*A01H 5/02* (2006.01)

(52) U.S. Cl.
CPC ..... *A01H 5/025* (2013.01)
USPC ..... Plt./360

(58) Field of Classification Search
USPC ..... Plt./360
See application file for complete search history.

(56) References Cited

PUBLICATIONS

UPOV Record Detail 'QZ' 2013.*
UPOV Record Detail 'NO' 2013.*

* cited by examiner

*Primary Examiner* — June Hwu
*Assistant Examiner* — Keith Robinson
(74) *Attorney, Agent, or Firm* — Cochran Freund & Young LLC; James M. Weatherly

(57) ABSTRACT

A new *Osteospermum* plant particularly distinguished by having violet ray florets and dark green leaves is disclosed.

1 Drawing Sheet

Genus and species: *Osteospermum ecklonis* Norl.
Variety denomination: 'KLEOE12190'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE12190'. 'KLEOE12190' originated from a cross-pollination between the proprietary female *Osteospermum* variety 'SU 10' (unpatented), having violet ray florets and a light green leaf color, and the proprietary male *Osteospermum* variety 'X 95' (unpatented), having purple to violet ray florets and a dark green flower color.

In the summer of 2008 the two *Osteospermum* parental lines 'SU 10' and 'X 95' were crossed in Stuttgart, Germany and seeds were obtained. The seeds were sown and plants were grown for evaluation. A plant line was selected in August 2009 which had violet ray florets and dark green leaves and named 'KLEOE12190'. In August 2009 'KLEOE12190' was first vegetatively propagated by vegetative cuttings. 'KLEOE12190' was found to reproduce true to type in successive generations of asexual propagation via terminal cuttings.

CROSS REFERENCE TO RELATED APPLICATIONS

Plant Breeder's Rights for 'KLEOE12190' were applied for in Canada on Feb. 8, 2013, Application No. 13-7921, the European Union on Jun. 21, 2013, Application No. 2013/1670, and in Norway on Aug. 5, 2013, Application No. 1307.

'KLEOE12190' has not been made publicly available or sold more than one year prior to the filing date of this application.

SUMMARY

The following are the most outstanding and distinguishing characteristics of this new variety when grown under normal horticultural practices in Stuttgart, Germany.

1. Violet rays florets; and
2. Dark green leaves.

DESCRIPTION OF THE PHOTOGRAPH

This new *Osteospermum* plant is illustrated by the accompanying photograph which shows a close-up of the flowers. The photograph is of a three-month-old plant grown in a controlled greenhouse environment in Stuttgart, Germany under greenhouse conditions in April 2012. The colors shown are as true as can be reasonably obtained by conventional photographic procedures.

DESCRIPTION OF THE NEW VARIETY

The following detailed descriptions set forth the distinctive characteristics of 'KLEOE12190'. The data which define these characteristics were collected from asexual reproductions carried out in Stuttgart, Germany. Data was collected on seven-month-old plants grown in a controlled greenhouse environment in Stuttgart, Germany under greenhouse conditions on Jan. 28, 2013. Color references are to The R.H.S. Colour Chart of The Royal Horticultural Society of London (R.H.S.), $5^{th}$ edition (2007).

Classification:
*Family*.—Compositae.
*Botanical*.—*Osteospermum ecklonis* Norl.
*Common*.—*Osteospermum*, African Daisy.
*Designation*.—'KLEOE12190'.

Parentage:
*Female parent*.—*Osteospermum* line 'SU 10' (unpatented).
*Male parent*.—*Osteospermum* line 'X 95' (unpatented).

Plant:
*Form and habit*.—Herbaceous perennial but usually cultivated as an annual.
*Growth habit*.—Upright.
*Branching habit*.—Freely branching.
*Height* (*from top of soil, including inflorescence*).—15.0 cm.
*Width* (*including inflorescences*).—20.0 cm.
*Propagation*.—Terminal cuttings.
*Time to produce a finished flowering plant*.—14 weeks.
*Time to initiate and develop roots*.—3 weeks.
*Root description*.—Freely rooting.
*Root color*.—Light tan in color.

Leaves:
*Arrangement*.—Alternate.
*Shape*.—Dentiform.
*Apex*.—Obtuse.
*Base*.—Acute.
*Margin*.—Medium.
*Immature color*.—Upper surface: RHS 143A. Lower surface: RHS 143B.
*Mature color*.—Upper surface: RHS 137A. Lower surface: RHS 137C.
*Length*.—About 7.0 cm.
*Width*.—About 4.0 cm.
*Texture*.—Upper surface: Leathery, smooth. Lower surface: Leathery, shiny.
*Petioles*.—Absent.
*Venation pattern*.—Pinnate.
*Venation color*.—Upper surface: RHS 138B. Lower surface: RHS 138B.
*Leaf variegation*.—Absent.

Stems:
*Total number of branches per plant* (*calculated at the base of the plant*).—About 5.
*Length*.—7.0 cm to 11.0 cm.
*Diameter*.—0.6 cm.
*Internode length*.—About 1.0 cm.
*Color*.—RHS 144B.
*Texture*.—Smooth.
*Anthocyanin*.—Absent.

Buds:
*Shape*.—Obovate.
*Length*.—About 1.0 cm.
*Diameter*.—About 1.0 cm.
*Color* (*at tight bud just before the ray florets unfold*).—RHS 143A.

Inflorescence:
*Type*.—Single.
*Blooming habit*.—Spring and autumn.
*Quantity of inflorescences per plant*.—20 to 30.
*Lastingness of the inflorescences on the plant*.—About 2 weeks.
*Fragrance*.—Absent to faint.
*Inflorescence diameter*.—About 5.5 cm.
*Inflorescence depth*.—About 1.0 cm.
*Disc diameter*.—1.5 cm.

Disc floret:
*Quantity per inflorescence*.—About 120.
*Type*.—Daisy.
*Shape*.—Lanceolate.
*Tube color*.—Closed: RHS 138B. Mature: RHS 83B.
*Length*.—0.6 cm.
*Diameter* (*at apex*).—0.1 cm.
*Apex*.—Obtuse.
*Apex color*.—RHS N88A.
*Base*.—Acute.
*Base color*.—RHS 145C.
*Margin*.—Entire.

Ray floret:
*Quantity per inflorescence*.—About 26.
*Shape*.—Oblanceolate.
*Color*.—Upper surface: RHS N87C. Lower surface: RHS N87D.
*Length*.—2.2 cm.
*Width*.—0.6 cm.
*Apex*.—Obtuse.
*Base*.—Acute.
*Margin*.—Entire.
*Texture*.—Upper surface: Smooth. Lower surface: Smooth, shiny.
*Peduncle*.—Length: 2.0 cm to 2.5 cm. Diameter: 0.2 cm. Texture: Rough. Color: RHS 143B.

Phyllaries:
*Texture*.—Smooth.
*Color*.—RHS 143A.
*Arrangement*.—Single.
*Observed quantity per plant*.—1 to 20.
*Shape*.—Lanceolate.
*Color*.—Upper surface: RHS 143A. Lower surface: RHS 143A.
*Length*.—1.2 cm.
*Width*.—0.2 cm.
*Apex*.—Acute.
*Base*.—Acute.
*Margin*.—Entire.
*Texture*.—Upper surface: Smooth. Lower surface: Smooth, rough.

Reproductive organs:
*Androecium*.—Location: On the disc floret. Stamens: Quantity: 5; fused into a single tube. Shape: Filamentous. Filament length: 0.5 cm. Filament diameter: Less than 0.05 cm. Anther: Shape: Lanceolate. Color: RHS N92A. Length: 0.2 cm. Diameter: Less than 0.05 cm. Pollen: Color: RHS 12A. Amount: Moderate.
*Gynoecium*.—Location: On the base of the petals (ray floret). Pistils: Number: About 26. Length: 0.4 cm. Diameter: Less than 0.05 cm. Stigma: Color: RHS 83A. Shape: Tapering, conical. Length: 0.2 cm. Diameter: Less than 0.05 cm. Style: Color: RHS 75B. Length: 0.2 cm. Diameter: Less than 0.05 cm.

Fruit and seed set: None observed.

Disease and pest/insect resistance: No particular disease or insect resistance observed.

COMPARISON WITH PARENTAL LINES AND KNOWN VARIETY

'KLEOE12190' is a distinct variety of *Osteospermum* having violet ray florets and dark green leaves; 'KLEOE12190' is distinguished from its parents as described in Table 1:

TABLE 1

| Comparison with Parental Lines | | | |
|---|---|---|---|
| Trait | 'KLEOE12190' | Female parent 'SU 10' (unpatented) | Male Parent 'X 95' (unpatented) |
| Ray floret color | Violet | Violet | Purple to violet |
| Color of leaves | Dark green | Lighter green | Dark green |

'KLEOE12190' is a distinct variety of *Osteospermum* having violet ray florets and dark green leaves. 'KLEOE12190' is most similar to the *Osteospermum* plant named 'FlowerPower Purple Blue' (unpatented). Differences between the two varieties are described in Table 2:

TABLE 2

| Comparison with Similar Variety | | |
|---|---|---|
| Trait | 'KLEOE12190' | Commercial line 'FlowerPower Purple Blue' (unpatented) |
| Color of ray florets | Violet | Purple-violet |

We claim:

1. A new and distinct variety of *Osteospermum* plant named 'KLEOE12190' as shown and described herein.

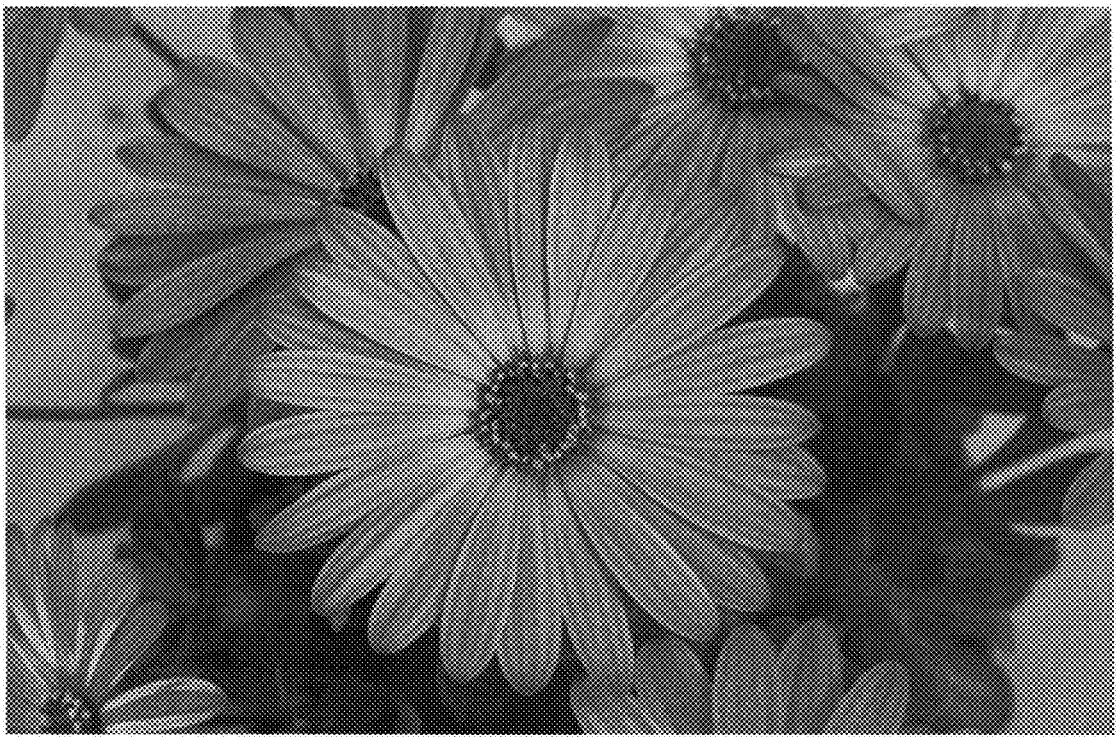

* * * * *